United States Patent [19]

Dean

[11] Patent Number: 5,206,392

[45] Date of Patent: Apr. 27, 1993

[54] FACILE SYNTHESIS OF ARYLMALEIC ACIDS AND ANHYDRIDES

[75] Inventor: William D. Dean, Arlington, Tex.

[73] Assignee: American Cyanamid Company, Wayne, N.J.

[21] Appl. No.: 873,846

[22] Filed: Apr. 27, 1992

[51] Int. Cl.⁵ .................... C07C 51/08; C07D 307/60
[52] U.S. Cl. .................................... 549/261; 549/253; 549/254; 558/373; 558/406; 562/465; 562/484
[58] Field of Search ................ 558/373, 406; 562/484; 549/261

[56] References Cited

U.S. PATENT DOCUMENTS 4,132,728  1/1979  Verbrugge et al. ................ 558/373

*Primary Examiner*—Bernard Dentz
*Attorney, Agent, or Firm*—Kenneth J. Dow

[57] ABSTRACT

A process for making acrylmaleic acid and arylmaleic anhydride derivative useful as intermediates for the preparation of arylmaleimides in the synthesis of compounds having activity in the central nervous system. The process involves reacting arylacetonitriles with glyoxylic acid to provide novel intermediate 3-aryl-3-cyanopropeneoates which may be converted to the arylmaleic acid and arylmaleic anhydride derivatives.

13 Claims, No Drawings

FACILE SYNTHESIS OF ARYLMALEIC ACIDS AND ANHYDRIDES

BACKGROUND OF THE INVENTION

1. Field of the Invention

The invention relates to a novel and facile process for making arylmaleic acid and arylmaleic anhydride derivatives, which are used as intermediates in the preparation of aryl-maleimides. The arylmaleimides are subsequently used to synthesize compounds which possess activity as antidepressants and as antistress agents in mammals.

2. Description of the Related Art

The Meerwein arylation of maleimides (Rondestvedt, C. S. Jr.; Vogl, O. *J. Amer. Chem. Soc.*, 1955, 77, 2313) or dialkylmaleates (Taylor, G. C., Strojny, E. J., *J. Amer. Chem. Soc.*, 1954, 76, 1872) is the most general method of making arylmaleic acid derivatives. Several factors preclude scaleup of the above reactions. In particular, the maleimides used are expensive and the arylations are always accompanied by a substantial quantity of aryl coupling to form biphenyls.

Another method explored involves a Wittig reaction of aroyl cyanides with carbalkoxymethylenetriphenylphosphoranes (Kalvode, L. *Coll. Czech. Chem. Comm.*, 1976, 41 2034). In our hands, the reaction of commercially available benzoyl cyanide with carboethyoxymethylenetriphenylphosphorane gives ethyl 3-cyano-3-phenylpropenoate as a 2.5:1 mixture of Z:E isomers. This ratio can be improved to about 10:1 Z:E by treatment of the mixture with thiophenol in refluxing toluene. The desired Z-cyanoester is then crystallized in hot formic acid to phenylmaleimide. Despite the overall efficiency, this method is impractical due to the lack of availability of the desired aroyl cyanides.

The prior art references are directed to laboratory scale synthesis. Attempts to produce the arylmaleic acid derivatives in a large scale according to the prior art procedures have proven to be unsatisfactory as detailed above.

This novel and facile process gives the arylmaleic acid derivatives in high yield. In addition, a highly pure product, a single geometric isomer, is obtained without the need for further purification, such as chromatography of the Z:E isomeric mixture.

SUMMARY OF THE INVENTION

The invention relates to a novel and facile process for making arylmaleic acid derivatives represented by formula I:

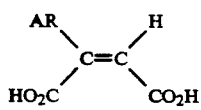

and aryl maleic anhydrides of the formula II:

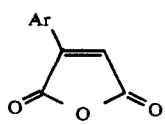

wherein Ar— is phenyl or substituted phenyl having one or more substituents selected from the group consisting of straight or branched chain $(C_1-C_4)$alkyl, $(C_1-C_3)$alkoxy, or halo selected from bromine, chlorine, fluorine or iodine; which comprises:

1) reacting a compound of the formula Ar—$CH_2CN$, wherein Ar— is hereinbefore defined; with glyoxylic acid hydrate in the presence of a sodium, potassium or cesium containing base, to yield an intermediate of formula III, wherein B is a salt selected from sodium, potassium or cesium; and

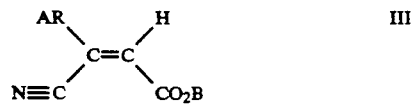

2) reacting a compound of formula III with a weak mineral acid at room temperature to yield arylmaleic acid derivative of Formula I or a strong mineral acid at reflux temperature to yield arylmaleic anhydrides of formula II.

DETAILED DESCRIPTION OF THE INVENTION

The present invention provides an efficient route to the synthesis of arylmaleic acid derivatives and arylmaleic anhydrides, for use as intermediates in the large scale preparation of arylmaleimides. The aryl maleimides may in turn be used to prepare compounds which have activity in the central nervous system as antidepressant and antistress agents (see McKenzie et al. U.S. Pat. No. 4,529,736). The arylmaleic anhydrides also have utility as Diels Alder dienophiles to provide cycloadducts which are useful in the preparation of various medicinal agents. They are also useful in copolymerization reactions, in manufacturing alkyd-type resins, dye intermediates and agriculturals such as maleic hydrazide and Malathion. The conversion of aryl maleic anhydrides to arylmaleimides is known from *Org. Synthesis*, Collected Vol. 5, John Wiley & Sons, 1973, p. 944; and Epstein et al., *J. Med. Chem.*, 1981, 24: 481–490.

The condensation of readily available arylacetonitriles with glycoxylic acid provides an easy route to 3-aryl-3-cyanopropenoates. Glyoxylic acid has been shown to condense readily with ketones under acidic (Reigh-Rohrwig, P. Raninger, F., Woerther, E. Kloimstein, E. *Ger. Offen.*, 2, 614, 827, 1977) or basic conditions (Pettit, G. R., Green, B. Dunn, G. L., *J. Org. Chem.*, 1970, 35, 1367) to provide acylacrylic acids or hydroxyacetic acids, respectively. The reaction of arylacetonitriles with glyoxylic acids is not reported in the literature.

The reaction of the arylacetonitrile with glycoxylic acid is generally carried out in an alcohol in the presence of a base. Suitable alcohols include methanol, ethanol, propanol or isopropanol and equivalents thereof. For example, condensations using an aqueous sodium hydroxide-methanol reaction medium, at room temperature, afford the corresponding sodium Z-3-aryl-3-cyanopropenoates in acceptable yield.

The base used in the condensations is a sodium, potassium or cesium containing base or equivalents thereof. The preferred bases are selected from sodium hydroxide, potassium carbonate or cesium carbonate. However, as shown in Table 1, best results are obtained by treatment of the arylacetonitiles 1 with 1.5–2.0 equivalents of glyoxylic acid hydrate in methanol and using potassium carbonate as the base.

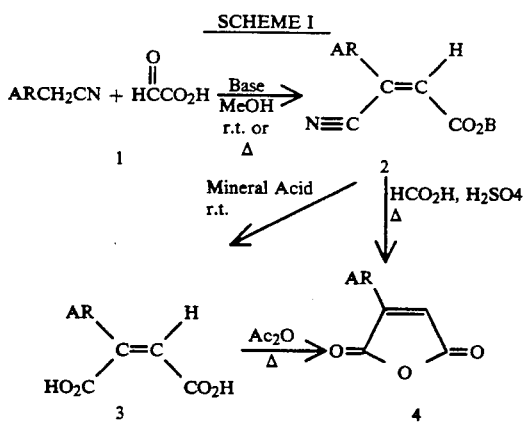

SCHEME I

In general, arylacetonitriles containing activating groups, such as halogen, react readily at room temperature. Phenylacetonitrile and nitriles containing electron donating groups, such as alkoxy, react best at reflux temperature. In all cases, the products, 2, precipitate from the reaction mixtures and are freed of the inorganic impurities by suspension in cold water.

All the condensation examined result in the formation of a single geometric isomer as evidenced by $H^1NMR$. The products are shown to be the desired Z-isomer by their cyclization in hot formic acid to the known arylmaleic anhydrides, 4, in good yield (Table II).

The arylmaleic acids, 3 may be prepared from the corresponding Z-3-aryl-3-cyano-propenoates, 2, by reaction at room temperature with a weak mineral acid such as 10%-25% aqueous hydrochloric acid. (Table III). The arylmaleic acids, 3, may be converted to the

TABLE I

Preparation of 2-3-aryl-3-cyanopropenoates (Formula III)

| | | Yield | | C | | H | | N | | |
|---|---|---|---|---|---|---|---|---|---|---|
| Ar | B | (%) | mp (°C.) | Calc | Found | Calc | Found | Calc | Found | H'-NMR (ppm) |
| a) $C_6H_5$ | K or Cs | 86 | 245 | 56.72 | 56.94 | 2.86 | 3.08 | 6.61 | 6.66 | 7.75(m, 5H), 7.28(br, s, 1H) |
| b) $4-BrC_6H_4$ | K | 94 | 252–253 | 41.40 | 41.14 | 1.74 | 1.49 | 4.83 | 4.81 | 7.8(q, 4H), 7.25(s, 1H) |
| c) $4-ClC_6H_4$ | K | 92 | 252–253 | 48.88 | 48.58 | 2.05 | 1.86 | 5.70 | 5.69 | 7.75(q, 4H), 7.3(s, 1H) |
| d) $3,4-Cl_2C_6H_3$ | K | 92 | 252 | 42.87 | 42.83 | 1.44 | 1.34 | 5.00 | 4.81 | 7.9(s, 1H), 7.70(m, 2H), 7.3(s, 1H) |
| e) $4-MeC_6H_4$ | K | 63 | 242 | 58.64 | 58.31 | 3.58 | 3.39 | 6.22 | 6.10 | 7.3–7.55(q, 4H), 7.04(s, 1H) 2.4(s, 3H) |
| f) $3-MeC_6H_4$ | K | 93 | 230 (dec) | 58.64 | 58.33 | 3.58 | 3.56 | 6.22 | 6.19 | 7.3–7.6(m, 4H), 7.15(s, 1H), 2.4(s, 3H) |
| g) $3,4,5-(MeO)_3C_6H_2$ | K or Cs | 26 | 199–200 | 38.81[a] | 39.03 | 3.01 | 2.79 | 3.48 | 3.41 | 6.99(s, H), 6.65(s, 2H), 3.85(s, 6H) 3.80(s, 3H) |
| h) $4-PhC_6H_5$ | K | 73 | 257 (dec) | 66.87 | 66.45 | 3.51 | 3.83 | 4.87 | 4.87 | 8.20–7.45(m, 9H), 7.05(s, 1H) |

[a] microanalysis of cesium salt

TABLE II

Preparation of Aryl Maleic Anhydrides (Formula II)

| Ar | Yield (%) | mp (°C.) | Lit mp (°C.) | H'NMR (ppm) |
|---|---|---|---|---|
| a) $C_6H_5$ | 48 | 120–121 | 119[c] | 8.1–7.95(m, 2H), 7.6(m, 3H), 7.10(m, 1H) |
| b) $4-BrC_6H_4$ | 81 | 156–157 | 156[d] | 7.8(q, 4H), 7.15(s, 1H) |
| c) $4-ClC_6H_4$ | 77 | 146–148 | 146[e] | 8.0–7.5(q, 4H), 7.08(s, 1H) |
| d) $3,4-Cl_2C_6H_3$ | 71 | 114.5–116 | 115–116[f] | 8.25–7.75(m, 3H), 7.01(s, 1H) |
| e) $4-MeC_6H_4$ | 31 | 109–110 | 108–111[e] | 7.95(d, 2H), 7.65(s, 1H), 7.35(d, 2H) |
| f) $3-MeC_6H_4$ | 31 | 89–90 | 88–90[g] | 7.8–7.3(m, 4H), 7.05(s, 1H), 2.95(s, 3H) |
| g) $3,4,5-(MeO)_3C_6H_2$[a] | 21 | 150–151 (toluene) | | 7.20(s, 2H), 6.90(s, 1H), 3.95(s, 9H) |
| h) $4-PhC_6H_4$[b] | 76 | 194.5–196 (chloroform) | | 8.15(d, 2H), 7.90(d, 2H), 7.79(s, 2H) 7.75(s, 1H), 7.6–7.4(m, 3H) |

[a] Microanalysis Calc; C: 59.09; H: 4.58 Found; C: 58.84, H: 4.1
[b] Microanalysis Calc; C: 76.79; H: 4.03 Found; C: 76.47, H: 4.15
[c] Taylor, G. C.; Strojny, E. J. J. Amer. Chem. Soc. 1954, 76, 1872.
[d] Neber, P. W. Annalen, 1930, 478, 197.
[e] Rondestvedt, C. S. Jr.; Vogl, O. J. Amer. Chem. Soc. 1955, 77, 2313.
[f] Cassella, L. D. B. P 870106, 1938.
[g] Hoch, J. Comptes Rendu, 1965, 261, 4132.

TABLE III

Preparation of Arylmaleic Acids (Formula I)

| | | | C | | H | | Halogen | | |
|---|---|---|---|---|---|---|---|---|---|
| Ar | Yield (%) | mp (°C.) | Calc | Found | Calc | Found | Calc | Found | H'-NMR (ppm) |
| b) $4-BrC_6H_4$ | 91 | 152–154 | 44.31 | 44.13 | 2.60 | 2.34 | 29.48 | 29.56 | 11.4(br. s, 2H), 7.45(q, 4H), 6.23(s, 1H) |
| c) $4-ClC_6H_4$ | 85 | 145–147 | 53.00 | 52.73 | 3.11 | 3.09 | 15.64 | 15.56 | 13.2(br. s, 2H), 7.6–7.48(q, 1H), 6.4(s, 1H) |
| e) $4-MeC_6H_4$ | 61 | 118–120 | 64.07 | 64.15 | 4.89 | 4.64 | | | 11.2(s, 2H), 7.5–7.1(q, 4H), 6.2(s, 1H), 2.33(s, 3H) |
| f) $3-MeC_6H_4$ | 59 | 108–110 | 64.07 | 64.09 | 4.89 | 4.93 | | | 7.2–7.4(m, 4H), 6.3(s, 1H), 2.38(s, 3H) | arylmaleic anhydrides, as stated, by treatment with hot formic acid or equivalents thereof.

The structures of the arylmaleic acids, 3, are confirmed by H¹NMR and by their conversion to the anhydrides, 4, using acetic anhydride.

The aryl maleic anhydrides, 4, may be prepared directly from the corresponding Z-3-aryl-3-cyano propenoates, 2, by reaction with a strong mineral acid, such as formic acid containing sulfuric acid at reflux temperature. (Table II)

The present invention demonstrates that arylacetonitriles and glyoxylic acid condense under mild conditions providing intermediates that can easily be converted to various useful arylmaleic acid derivatives. The ease of the reaction sequence, as well as the availability of the starting arylacetonitriles, makes this route a useful alternative to published procedures for the large scale synthesis of the arylmaleic acid derivatives.

This invention will be described in greater detail in conjunction with the following examples.

EXAMPLE 1

General Procedure for the Condensation of Arylacetonitiles with Glyoxylic Acid

A solution of 0.05 mole of the appropriate arylacetonitrile, 1, (b-d), 0.075 mole of glyoxylic acid hydrate and 0.127 mole of potassium carbonate dissolved in 100 ml of methanol is stirred at room temperature for 3-5 hours. The resulting thick solid precipitate is collected, washed with dichloromethane and resuspended in 500 ml of cold water. The suspension is stirred overnight, collected and air dried to give the corresponding potassium Z-3-aryl-3-cyanopropenoates, 2 (b-d). These products were sufficiently pure for further transformations. Analytically pure samples of 2 are obtained when recrystallized from water. See Table I for the physical data of the compounds listed below.

(2b) (E)-3-(4-Bromophenyl)-3-cyano-2-propenoic acid potassium salt (2c) (Z)-3-(4-Chlorophenyl)-3-cyano-2-propenoic acid potassium salt (2d) (Z)-3-Cyano-3-(3,4-dichlorophenyl)-2-propenoic acid potassium salt

EXAMPLE 2

Condensation of Arylacetonitriles with Glyoxylic Acid

The condensation is performed as described in Example 1 with the reaction solution being heated at reflux temperature for 2-24 hours. The corresponding Z-3-aryl-3-cyanopropenoates, 2 (a, e-h), are isolated by filtration after cooling the reaction mixture. See Table I for the physical data of the compounds listed below:

(2a) (Z)-3-Cyano-3-phenyl-2-propenoic acid potassium salt (2e) (Z)-3-Cyano-3-(4-methylphenyl)-2-propenoic acid potassium salt (2f) (Z)-3-Cyano-3-(3-methylphenyl)-2-propenoic acid potassium salt (2g) (Z)-3-Cyano-3-(3,4,5-trimethylphenyl)-2-propenoic acid potassium salt (2h) 3-[1,1'-Biphenyl]-4-yl-3-cyano-2-propenoic acid potassium salt

EXAMPLE 3

Cyclization of Potassium Z-3-Aryl-3-cyanopropenoates to Arylmaleic Anhydrides

The potassium Z-3-aryl-3-cyanopropenoates (0.094 mole), 2 (a-h), are dissolved in 200 ml of 88% formic acid containing 15 ml of concentrated sulfuric acid. The reaction mixtures are heated at reflux temperature for 2-3 hours, cooled and poured into ice water. The resulting solids are collected, washed with water, and air dried to give the desired arylmaleic anhydride, 4 (a-h).

The products are of sufficient purity for use in subsequent reactions. See Table II for the physical data of the compounds listed below.

(4a) Phenyl maleic anhydride
(4b) (4-Bromophenyl)-2,5-furandione
(4c) (4-Chlorophenyl)2,5-furandione
(4d) 3-(3,4-Dichlorophenyl)-2,5-furandione
(4e) p-Tolyl-maleic anhydride
(4f) (3-Methylphenyl-2,5-furandione
(4g) 3-(3,4,5-Trimethoxyphenyl)-2,5-furandione
(4h) 3-[1,1'-Biphenyl]-4-yl-2,5-furandione

EXAMPLE 4

Preparation of Arylmaleic Acids

The potassium Z-3-aryl-3-cyanopropenoates (0.012 mole), 2 (b,c,e,f) are suspended in 300 ml of 10% hydrochloric acid. The reaction mixture is stirred at room temperature overnight, the solid is collected, washed with water, and air dried to give analytically pure arylmaleic acids, 3 (b,c,e,f). See Table III for the physical data of the compounds listed below.

(3b) (Z)-(4-Bromophenyl)-2-butenedioic acid
(3c) (Z)-(4-Chlorophenyl)-2-butenedioic acid
(3d) (Z)-(4-Methylphenyl)-2-butenedioic acid
(3e) (Z)-(3-Methylphenyl)-2-butenedioic acid
(3f) (Z)-(3-Methylphenyl)-2-butenedioic acid

We claim:
1. A process for preparing compounds of the formula III:

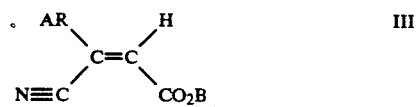

wherein Ar is phenyl or substituted phenyl having one or more substituents selected from the group consisting of straight or branched chain ($C_1$-$C_4$) alkyl, ($C_1$-$C_3$) alkoxy, or halo selected from bromine, chlorine, fluorine or iodine, and B is a salt selected from sodium, potassium or cesium, which comprises:

reacting a compound of the formula Ar—$CH_2CN$, wherein Ar is as defined above, with glyoxylic acid hydrate in the presence of a sodium, potassium or cesium containing base to yield the compound of formula III.

2. A process for preparing compounds of formula I:

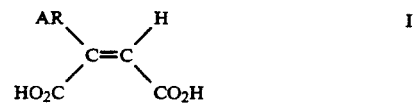

wherein Ar— is phenyl or substituted phenyl having one or more substituents selected from the group consisting of straight or branched chain ($C_1$–$C_4$)alkyl, ($C_1$–$C_3$)alkoxy, or halo selected from bromine, chlorine, fluorine or iodine; which comprises:

(a) reacting a compound of the formula Ar—$CH_2CN$, wherein Ar— is hereinabove defined; with glyoxylic acid hydrate in the presence of a sodium, potassium or cesium containing base to yield an intermediate of formula III wherein B is a salt selected from sodium, potassium or cesium; and

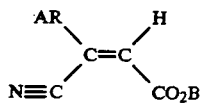     III (b) reacting a compound of formula III with a weak mineral acid at room temperature to yield arylmaleic acid derivatives of Formula I.

3. A process for preparing compounds of formula II:

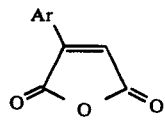     II wherein Ar is phenyl or substituted phenyl having one or more substituents selected from the group consisting of straight or branched chain ($C_1$–$C_4$) alkyl, ($C_1$–$C_3$) alkoxy, or halo selected from bromine, chlorine, fluorine or iodine; which comprises:

(a) reacting a compound of the formula Ar—$CH_2$—CN, wherein Ar is as defined above, with glyoxylic acid hydrate in the presence of a sodium, potassium or cesium containing base to yield an intermediate of formula III wherein B is a salt selected from sodium potassium or cesium; and

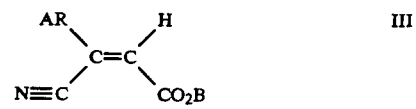     III (b) reacting the compound of formula II with a strong mineral acid at reflux temperature.

4. The process of claim 1 wherein the reaction is carried out in an alcohol selected from methanol, ethanol, propanol or isopropanol.

5. The process of claim 4 wherein the alcohol is methanol.

6. The process of claim 1 wherein the base is selected from sodium hydroxide, potassium carbonate or cesium carbonate.

7. The process of claim 6 wherein the base is potassium carbonate.

8. The process of claim 2 wherein said mineral acid is selected from hydrochloric acid or hydrobromic acid.

9. The process of claim 8 wherein the mineral acid is 25% hydrochloric acid.

10. The process of claim 2 wherein the compound of Formula I is (Z)-(4-Bromophenyl)-2-butanedioic acid.

11. The process of claim 2 wherein the compound of Formula I is (Z)-(4-Chlorophenyl)-2-butenedioic acid.

12. The process of claim 2 wherein the compound of Formula I is (Z)-(3-Methylphenyl)-2-butenedioic acid.

13. The process of claim 2 wherein the compound of Formula I is (Z)-(4-Methylphenyl)-2-butenedioic acid.

* * * * *